US010401300B2

(12) United States Patent
Otani et al.

(10) Patent No.: US 10,401,300 B2
(45) Date of Patent: Sep. 3, 2019

(54) DEFECT OBSERVATION METHOD AND DEVICE AND DEFECT DETECTION DEVICE

(71) Applicant: HITACHI HIGH-TECHNOLOGIES CORPORATION, Minato-ku, Tokyo (JP)

(72) Inventors: Yuko Otani, Tokyo (JP); Yuta Urano, Tokyo (JP); Toshifumi Honda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 166 days.

(21) Appl. No.: 15/317,065

(22) PCT Filed: May 27, 2015

(86) PCT No.: PCT/JP2015/065318
§ 371 (c)(1),
(2) Date: Dec. 7, 2016

(87) PCT Pub. No.: WO2015/198781
PCT Pub. Date: Dec. 30, 2015

(65) Prior Publication Data
US 2017/0108444 A1    Apr. 20, 2017

(30) Foreign Application Priority Data

Jun. 26, 2014    (JP) ................................. 2014-131382

(51) Int. Cl.
*G01B 21/00*    (2006.01)
*G01N 21/88*    (2006.01)
(Continued)

(52) U.S. Cl.
CPC ..... *G01N 21/8806* (2013.01); *G01B 11/0608* (2013.01); *G01B 11/2513* (2013.01);
(Continued)

(58) Field of Classification Search
CPC ........... G01N 21/8806; G01N 21/9505; G01N 2223/418; G01B 11/2513; G01B 11/2527; G02B 21/26
See application file for complete search history.

(56) References Cited

U.S. PATENT DOCUMENTS

2011/0194101 A1* 8/2011 Tachizaki ........... G01N 21/9501
356/72
2012/0274391 A1 11/2012 Otani et al.
(Continued)

FOREIGN PATENT DOCUMENTS

JP    2001-100104 A    4/2001
JP    2007-225563 A    9/2007
(Continued)

OTHER PUBLICATIONS

Kudo, Ryota et al.; "Super-Resolution Optical Inspection for Semiconductor Defects Using Standing Wave Shift:—Basic Function Verification of Experimental Equipment for Super-Resolution with Coherent Image Reconstruction"; 2013; Nendo Seimitsu Kogakukai Shunki Taikai Gakujutu Koenkai Koen Ronbunshu; pp. 373-374.

Primary Examiner — Maurice C Smith
(74) Attorney, Agent, or Firm — Miles & Stockbridge PC

(57) ABSTRACT

A defect observation method for observing a defect on a sample detected by another inspection device with a scanning electron microscope including the steps of: optically detecting the defect using the position information for the defect: illuminating the sample including the defect with an illumination intensity pattern having periodic intensity variation in two dimensions by irradiating a plurality of illumination light beams onto the surface of the sample while phase modulating the light beams in a single direction and successively moving the light beams in small movements in a direction different from the single direction, imaging the surface of the sample that is illuminated by the
(Continued)

illumination intensity pattern having periodic intensity variation in two dimensions and includes the defect detected by the other inspection device, and detecting the defect detected by the other inspection device from the image obtained through the imaging of the surface of the sample.

8 Claims, 9 Drawing Sheets

(51) Int. Cl.

| | |
|---|---|
| *G01B 11/30* | (2006.01) |
| *G01N 21/956* | (2006.01) |
| *G01B 11/06* | (2006.01) |
| *G01N 21/95* | (2006.01) |
| *G01N 23/2251* | (2018.01) |
| *G02B 21/00* | (2006.01) |
| *G02B 21/10* | (2006.01) |
| *G02B 21/26* | (2006.01) |
| *G02B 27/09* | (2006.01) |
| *G02B 27/58* | (2006.01) |
| *G01B 15/08* | (2006.01) |
| *G01B 11/25* | (2006.01) |
| *G03F 7/20* | (2006.01) |

(52) U.S. Cl.
CPC .......... *G01B 11/2527* (2013.01); *G01B 11/30* (2013.01); *G01B 15/08* (2013.01); *G01B 21/00* (2013.01); *G01N 21/9501* (2013.01); *G01N 21/956* (2013.01); *G01N 23/2251* (2013.01); *G02B 21/0016* (2013.01); *G02B 21/10* (2013.01); *G02B 21/26* (2013.01); *G02B 27/0933* (2013.01); *G02B 27/58* (2013.01); *G03F 7/7065* (2013.01); *G01B 2210/56* (2013.01); *G01N 2021/8822* (2013.01); *G01N 2021/8825* (2013.01); *G01N 2021/8861* (2013.01); *G01N 2021/8867* (2013.01); *G01N 2201/068* (2013.01); *G01N 2223/33* (2013.01); *G01N 2223/418* (2013.01); *G01N 2223/6116* (2013.01); *G01N 2223/646* (2013.01)

(56) References Cited

U.S. PATENT DOCUMENTS

2012/0274931 A1* 11/2012 Otani ..................... G01N 21/21
356/237.3
2015/0003722 A1   1/2015 Otani et al.

FOREIGN PATENT DOCUMENTS

| JP | 2011-106974 A | 6/2011 |
|---|---|---|
| JP | 2012-13614 A | 1/2012 |
| WO | WO 2013/118351 A1 | 8/2013 |

* cited by examiner

F I G. 1
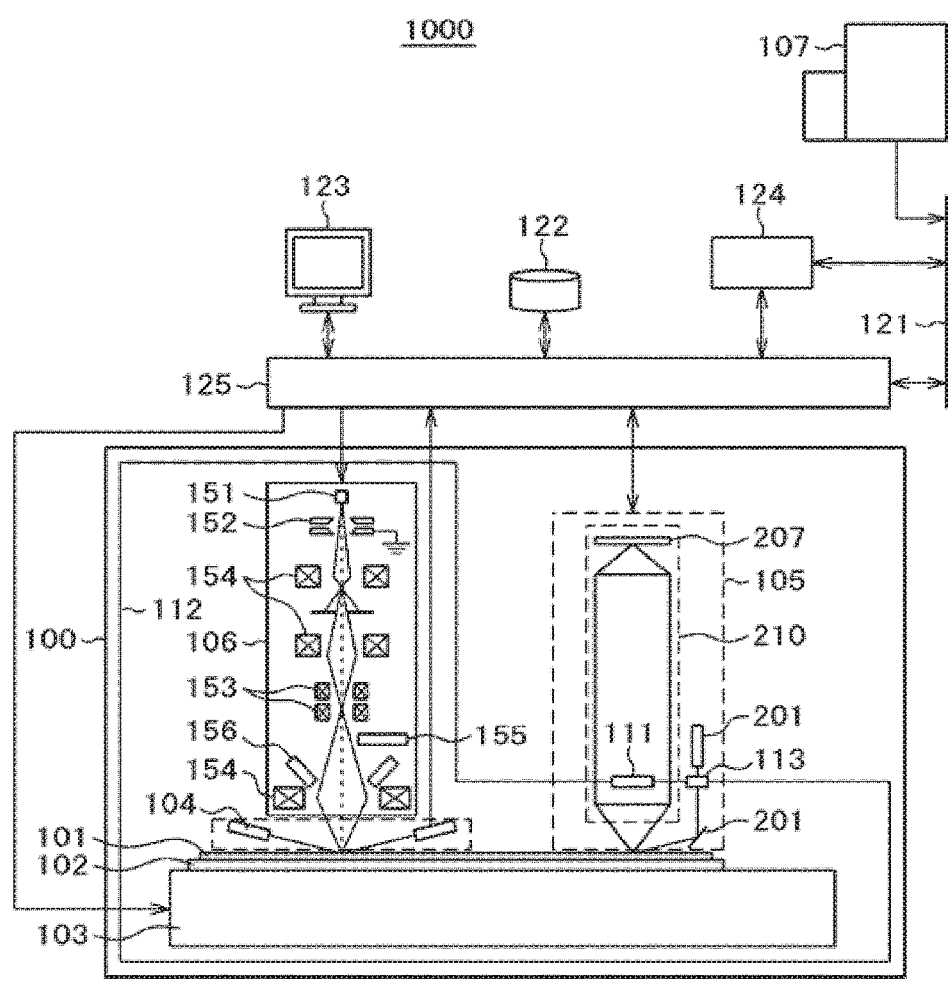

F I G. 2
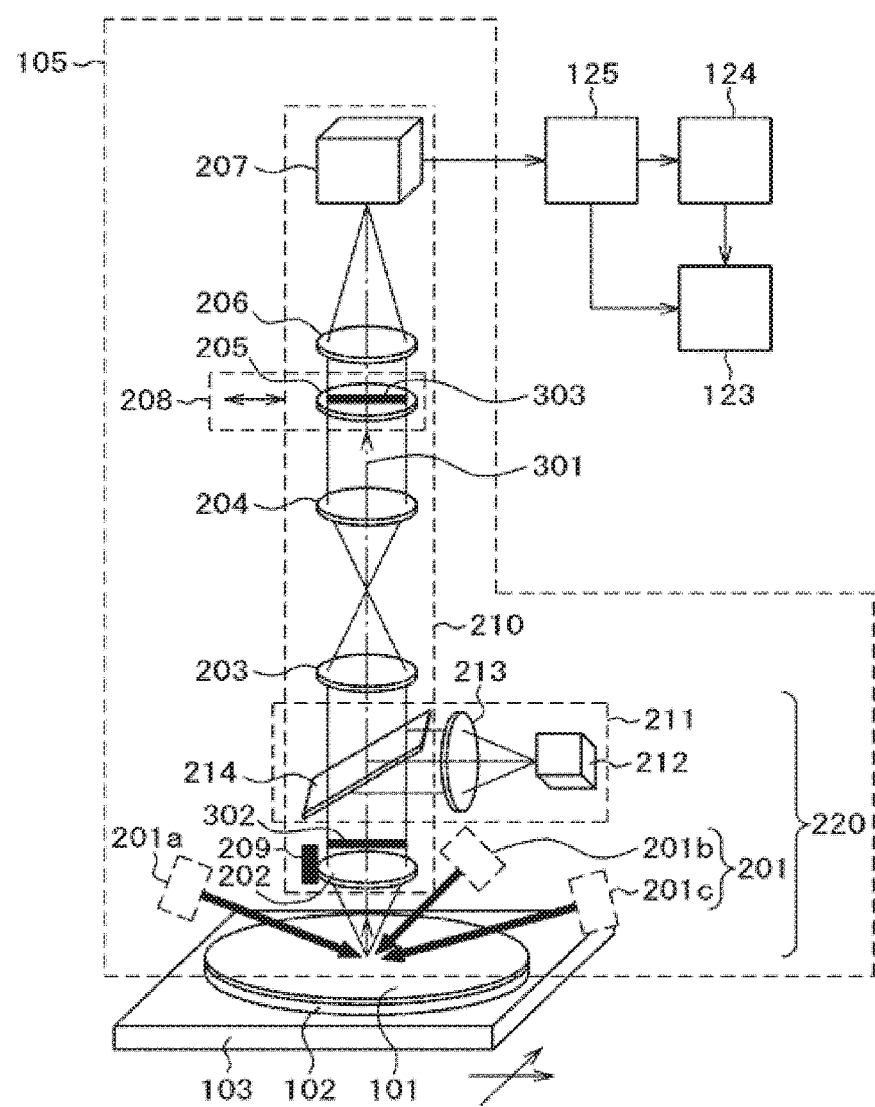

F I G. 4
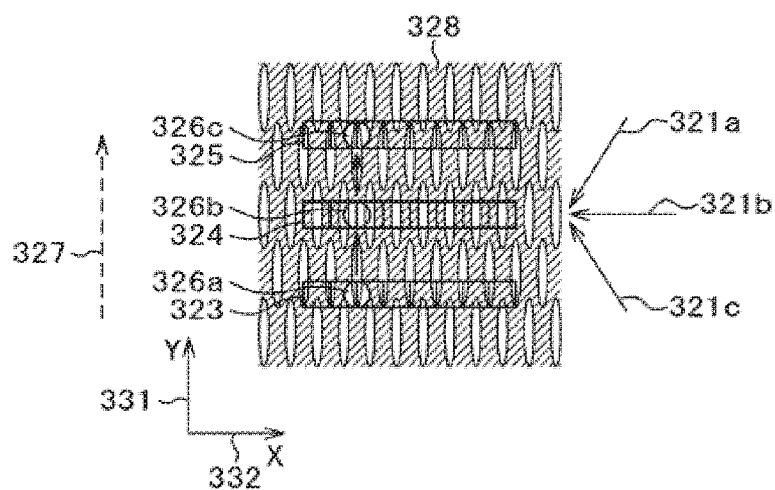

DEFECT OBSERVATION METHOD AND DEVICE AND DEFECT DETECTION DEVICE

TECHNICAL FIELD

The present invention relates to a defect observation method for enabling the quick, high-resolution observation of a defect or the like generated on a semiconductor wafer in a semiconductor device production process, a device for the defect observation, and a defect detection device.

BACKGROUND ART

In the semiconductor device production process, a pattern defect (hereinafter, referred to as defect including foreign matter and pattern defect), for example, the foreign matter, short-circuit, disconnection on the semiconductor substrate (wafer) may cause such failure as insulation failure and short-circuit of wiring. As the circuit pattern formed on the wafer is micronized, the resultant micronized defect may cause capacitor insulation failure, and destruction of gate oxide. Those defects are caused by multiple factors mixed in various states from the movable part of the carrier device and the human body, those produced through reaction of the process gas inside the treatment device, and mixture in chemicals and materials. It is therefore important to detect the defect generated in the production process, locate the source of the defect as soon as possible, and prevent generation of the defect for successful mass production of the semiconductor devices.

In the past, the method of locating the cause of the defect has been implemented by allowing the defect detection device to specify the defect position, observing and classifying the defect in detail by means of an SEM (Scanning Electron Microscope) or the like, and comparing the result with the database so as to estimate the cause of the defect.

The device for observing the defect in detail by means of the SEM as disclosed in Patent Literature 1 is configured to detect the position of the defect on the sample by the optical microscope installed in the SEM-type defect observation device using the position information of the defect on the sample detected by an additional defect inspection device, correct the position information of the defect detected by the additional inspection device, and observe (review) the defect in detail by the SEM-type defect observation device.

Along with the higher integration of the semiconductor device, the pattern to be formed on the wafer becomes further micronized. Accordingly, the defect critical for the semiconductor device is also micronized. The aforementioned micronized defect detected by the defect inspection device is required to be observed (reviewed) with the SEM-type defect observation device in detail without lowering throughput. In order to implement the aforementioned observation, it is necessary to allow the optical microscope installed in the SEM-type defect observation device to detect the defect which has been detected by the additional defect inspection device quickly with high accuracy, and to correct the position information detected by the additional defect inspection device.

Patent Literature 2 discloses dark-field type microscopic method as the technique for detecting the micronized defect with high accuracy. For example, the method is designed to improve horizontal resolution around the interface using standing evanescent light as the illumination light beam, and actualize the resolving power higher than that of the generally employed optical method while retaining the throughput derived therefrom.

CITATION LIST

Patent Literature

PTL 1: Japanese Patent Application Laid-Open No. 2011-106974
PTL 2: Japanese Patent Application Laid-Open No. 2007-225563

SUMMARY OF INVENTION

Technical Problem

Patent Literature 1 discloses the SEM-type defect inspection device which allows the optical microscope installed therein to detect the defect that has been detected by the additional inspection device, and corrects the defect position information so that the SEM-type defect observation device observes (reviews) the defect in detail. However, it does not disclose the structure of the optical microscope adapted to quickly detect the more micronized defect with high accuracy.

Meanwhile, Patent Literature 2 discloses the microscope system configured to use the standing wave pattern generated by interference as a result of irradiation of two light beams onto the sample from the opposite directions as illumination light, allow the sensor to trap the light generated from the sample in reference to the set standing wave pattern, and convert the trapped light into the electric signal by which the sample is observed. The microscope system modulates the standing wave pattern by changing the relative optical path lengths between the two light beams, acquires the sensor signal resulting from the light generated from the sample for each different illumination state, and generates the high resolution signal using the plurality of acquired signals.

In the past, the microscope system as disclosed in Patent Literature 2 is required to illuminate the sample with the standing wave pattern having periodic intensity variation in two directions (hereinafter, referred to as X-direction, Y-direction) which, at least, are not parallel to each other, and to allow the respective standing wave patterns to shift the illumination intensity distribution parallel to directions each with the periodic intensity variation. The above configuration needs the optical system for generating the standing wave patterns both in the X-direction and the Y-direction, and the mechanism for modulating the standing wave pattern, respectively. Alternatively, the configuration needs the mechanism for rotating the sample or the incident direction of the illumination.

Accommodation of the interference optical system, and the standing wave pattern modulation mechanism in the respective X-direction and the Y-direction may enlarge the device, and increase the cost as a whole. The time period for switching the illumination direction is required in addition to the time period for imaging. In the case where the sample or the incident direction of the illumination light is rotated, the device may further be enlarged, and the cost is increased, requiring the time period for rotation.

It is an object of the present invention to provide a defect observation device, a defect observation method, and a defect inspection device, which attains high resolution of the defect detection in two-dimensional direction, and improves the defect detection throughputs without changing the relative incident azimuth of the illumination with respect to the sample.

Solution to Problem

Aiming at addressing the above-described problems, the present invention provides a defect observation method of optically detecting a defect on a sample, detected by an additional inspection device using position information of the defect, correcting the position information of the detected defect, and observing the defect by a scanning electron microscope using the corrected position information. The optical detection of the defect using the position information of the defect on the sample detected by the additional inspection device is implemented by illuminating the sample with an illumination intensity pattern having a periodic intensity variation in a two-dimensional direction by executing phase modulation of a plurality of illumination lights in one direction on a surface of the sample having the defect, and slightly shifting sequentially in a direction different from the one direction to irradiate the sample surface, imaging the surface of the sample having the defect detected by the additional inspection device, which is illuminated with the illumination intensity pattern having periodic intensity variation in the two-dimensional direction, and detecting the defect which has been detected by the additional inspection device from an image derived from imaging the sample surface.

Aiming at addressing the above-described problems, the present invention provides a defect observation device which includes an optical microscope which optically detects a defect on a sample surface using position information of the defect detected by an additional inspection device, a storage unit which corrects the position information of the defect on the sample detected by the additional inspection device, and stores the corrected information, and a scanning electron microscope which observes the defect using the corrected position information stored in the storage unit. The optical microscope includes an illumination unit which illuminates the sample surface having the defect with a plurality of illumination lights phase modulated in one-direction, a spatial modulation unit which slightly shifts the plurality of illumination lights sequentially in a direction different from the one-direction, an imaging unit which images the sample surface having the defect, which is illuminated with an illumination intensity pattern having periodic intensity variation in a two-dimensional direction by the illumination unit and the spatial modulation unit, and a defect detection unit which detects the defect detected by the additional inspection device by processing an image of the sample surface, which has been imaged by the imaging unit.

Aiming at addressing the above-described problems, the present invention provides a defect detection device for optically detecting a defect on a sample, which includes an illumination unit which illuminates a surface of a sample with a plurality of illumination lights phase modulated in one direction, a spatial modulation unit which slightly shifts the plurality of illumination lights sequentially in a direction different from the one direction, an imaging unit which images the sample surface having the defect, which is illuminated with an illumination intensity pattern having periodic intensity variation in a two-dimensional direction by the illumination unit and the spatial modulation unit, and a defect detection unit which detects the defect on the sample surface by processing an image of the sample surface imaged by the imaging unite.

Advantageous Effects of Invention

The present invention ensures to improve the resolution and throughput of the defect detection in the two-dimensional direction using light beams, and also ensures to improve throughput and resolution for the detailed defect observation using the SEM.

BRIEF DESCRIPTION OF DRAWINGS

FIG. 1 is a block diagram of an entire structure of a defect observation device according to a first example of the present invention.

FIG. 2 is a perspective view schematically illustrating an optical microscope of the defect observation device according to the first example of the present invention.

FIG. 4 is a plan view of a sample, indicating an illumination intensity distribution on the sample surface by the dark-field illumination of the optical microscope according to the first example of the present invention.

DESCRIPTION OF EMBODIMENTS

Figure 3A:
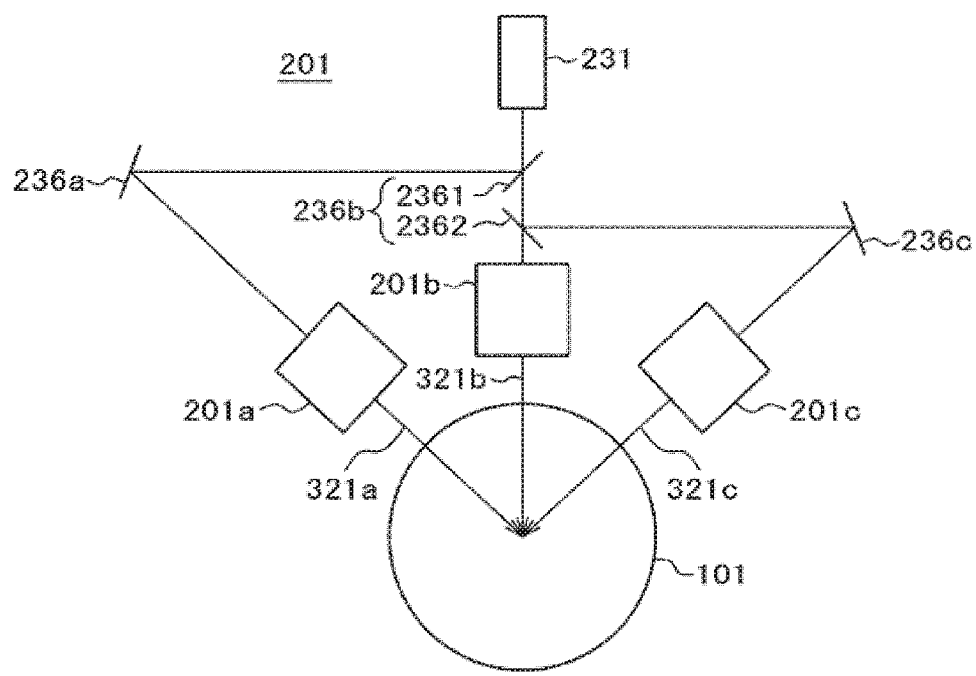
FIG. 3A is a block diagram schematically illustrating a dark-field illumination optical system of the optical microscope according to the first example of the present invention.

Examples of the present invention will be described referring to the drawings.

Example 1

FIG. 1 is a view showing a structure of a defect observation device according to a first example of the present invention. A defect observation device 1000 includes a review device 100, a network 121, a database 122, a user interface 123, a storage device 124, and a control system 125. The defect observation device 1000 is connected to a defect inspection device 107 as an additional inspection device via the network 121.

The defect inspection device 107 detects a defect that exists on a sample 101, and acquires defect information with respect to a position coordinate and a size of the defect. The defect inspection device 107 may be arbitrarily configured so long as the information about the defect on the sample 101 can be acquired.

The defect information acquired by the defect inspection device 107 is input to the storage device 124 or the control system 125 via the network 121. The storage device 124 stores the defect information acquired by the defect inspection device 107, which has been input via the network 121. The control system 125 reads the defect information input from the defect inspection device 107, or the defect information stored in the storage device 124, and controls the review device 100 based on the read defect information. Some or all of the defects detected by the defect inspection device 107 are observed in detail for classification of the defect, analysis of cause of the defect and the like.

The structure of the review device 100 as shown in FIG. 1 will be described.

The review device 100 includes a drive unit having a sample holder 102 and a stage 103, an optical height detector 104, an optical microscope 105, a vacuum tank 112, an SEM (Scanning Electron Microscope) 106 (electron microscope), and a laser displacement gauge (not shown). The sample 101 is placed on the sample holder 102 disposed on the movable stage 103. The stage 103 carries the sample 101 placed on the sample holder 102 between the optical microscope 105 and the SEM 106. As the stage 103 moves, the observation defect which exists on the sample 101 is positioned in the view of the SEM 106, or in the view of the optical microscope 105.

The control system 125 is connected to the stage 103, the optical height detector 104, the optical microscope 105, the SEM 106, the user interface 123, the database 122, and the storage device 124 for controlling operations and inputs of the respective components, for example, movement of the stage 103, modulation of the illuminating state and image acquisition performed by the optical microscope 105, image acquisition by the electron microscope 106, and measurement and the like performed by the measurement unit having the optical height detector 104. The control system 125 is connected to the high-order system (for example, defect inspection device 107) via the network 121.

The optical microscope 105 includes an optical irradiation system 220 having a dark-field illumination optical system 201 and a bright-field illumination optical system 211, and an optical detection system constituted by a detection optical system 210. A part of the optical microscope 105 (for example, an objective lens 202 and the like, see FIG. 2) is disposed inside the vacuum tank 112 for guiding the light to a detector 207 via vacuum sealing windows 111, 113 formed in the vacuum tank 112 for transmitting the light beam.

The control system 125 reads the defect information output from the defect inspection device 107, or the defect information stored in the storage device 124 so that the defect is detected again using the image information acquired by controlling the optical microscope 105 based on the read defect information, and the position information of the detected defect is output.

The control system 125 derives the defect coordinate difference between the defect inspection device 107 and the review device 100 based on the defect information output from the defect inspection device 107 and the defect information detected using the optical microscope 105, and corrects the defect position information stored in the storage device 124, which has been output from the defect inspection device 107.

The SEM 106 includes an electron irradiation system having an electron beam source 151, a lead-out electrode 152, a deflecting electrode 153, and an objective lens electrode 154, and an electron detection system having a secondary electron detector 155 and a reflection electron detector 156.

A primary electron emitted from the electron beam source 151 of the SEM 106 is subjected to beam-like lead-out process executed by the lead-out electrode 152, and accelerated. The trajectory of the accelerated primary electron beam is controlled by the deflecting electrode 153 in X-direction and Y-direction. The objective lens electrode 154 converges the primary electron beam having the trajectory controlled on the surface of the sample 101, which is then irradiated and scanned.

The secondary electron, reflection electron and the like are generated on the surface of the sample 101 irradiated with the primary electron beam and scanned. The secondary electron detector 155 detects the generated secondary electron, and the reflection electron detector 156 detects the electron with relatively higher energy such as reflection electron. A shutter (not shown) disposed on the optical axis of the SEM 106 selects start/stop of irradiation of the sample 101 with the electron beam emitted from the electron beam source 151.

The above-structured SEM 106 is controlled by the control system 125 to change the electron beam focus and the observation magnification. The SEM 106 reads the defect information output from the defect inspection device 107, defect information output from the optical microscope 105, the defect information stored in the storage device 124, or the defect information corrected by the control system 125, and observes the defect in detail based on the read defect information.

The optical height detector 104 serving as a measurement unit for the review device 100 measures the value corresponding to displacement on the surface of the observation region. The displacement includes various parameters such as the position of the observation region, amplitude of oscillation, frequency, and cycle. Specifically, the optical height detector 104 measures the height position of the surface of the observation region of the sample 101 on the stage 103, and oscillation in the direction perpendicular to the surface of the observation region. The displacement and oscillation measured by the optical height detector 104 will be output to the control system 125 as the signal.

Based on the defect information acquired by the defect inspection device 107, the control system 125 allows the optical microscope 105 to detect the defect again so as to convert the position information of the defect detected by the defect inspection device 107 into the position information on the review device. Using the defect position information on the review device converted from the defect position information on the inspection device 107, the SEM 106 allows the control system 125 to observe the defect converted into the position information on the review device.

FIG. 2 illustrates a structure example of the optical microscope 105.

The optical microscope 105 includes the optical illumination system 220 provided with the dark-field illumination optical system 201 having illumination systems 201a to 201c, and the bright-field illumination optical system 211, and the detection optical system 210. FIG. 2 omits description of the vacuum tank 112 and the vacuum sealing windows 111, 113.

As FIG. 3A shows, the dark-field illumination optical system 201 includes an illumination light source 231, a beam split section 236b, mirrors 236a, 236c, and illumination systems 201a, 201b, 201c.

In the dark-field illumination optical system 201, the light (laser) emitted from the illumination light source 231 is incident on the beam split section 236b including a reflector 2361 which reflects ⅓ of the incident light, and transmits ⅔ thereof, and a half mirror 2362 which transmits ½ of the incident light, and reflects ½ thereof. The reflector 2361 reflects ⅓ of the light, which proceeds toward the mirror 236a. The light reflects on the mirror 236a, and is incident on the illumination system 201a. Meanwhile, the light transmitting through the reflector 2361 is incident on the half mirror 2362, having ½ of which transmitting through the half mirror 2362, and another ½ of which reflected by the half mirror 2362. The light transmitting through the half mirror 2362 is incident on the illumination system 201b. The light reflected by the half mirror 2362 is further reflected by the mirror 236c and incident on the illumination system 201c.

As the dark-field illumination optical system 201 is configured as shown in FIG. 3A, the illumination light (laser) emitted from the illumination light source 231 is split into three beams, which are irradiated from the illumination systems 201a to 201c to the same region on the sample 101 as illumination lights 321a, 321b, 321c each with substantially the same intensity (amount of light), respectively. At this time, the illumination lights 321a, 321b, 321c emitted from the illumination systems 201a to 201c have different incident planes. The incident plane refers to the plane perpendicular to the surface of the sample 101, including the optical axis of the illumination light incident on the sample 101.

In the structure as described above, the reflector 2361 reflects ⅓ of the incident light, and transmits ⅔ thereof. It is possible to have the half-mirror configured to allow the reflector 2361 to reflect ½ of the incident light, and transmit ½ thereof so that each amount of the illumination lights 321a, 321b, 321c emitted from the illumination systems 201a to 201c for irradiation to the same region on the sample 101 differs from one another.

Figure 3B:
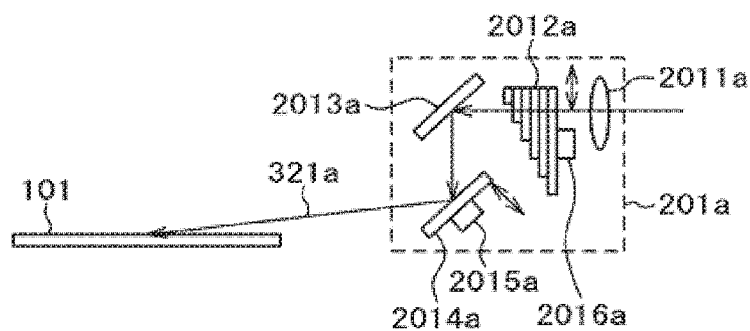
FIG. 3B is a block diagram schematically illustrating an illumination system of the dark-field illumination optical system according to the first example of the present invention.

Basically, as each of the illumination systems 201a, 201b and 201c has the same structure, FIG. 3B only shows the structure of the illumination system 201a.

The illumination system 201a includes a lens system 2011a, parallel flat plate 2012a formed by laminating glass plates each having the different length, mirrors 2013a, 2014a, and piezo elements 2015a, 2016a. The lens system 2011a controls the beam diameter and condensing NA of the illumination light reflected by the mirror 236a and incident on the illumination system 201a. The parallel flat plate 2012a is driven by the piezo element 2016a in the arrow direction at right angles to the optical path of the illumination light so as to stepwise change the optical path length of the illumination light transmitting through the parallel flat plate 2012a. The mirror 2014a is driven by the piezo element 2015a in the arrow direction, and oscillated at the desired frequency so that the optical path length of the reflecting illumination light is periodically changed.

The plurality of illumination lights irradiated to the surface of the sample 101 in different incident planes (illumination light 321a as shown in FIG. 3B) interfere with one another on the sample 101 so that the interference pattern with periodic intensity variation is generated. The interference pattern generates scattered light from the irradiation region on the sample 101.

As FIG. 2 shows, the bright-field illumination optical system 211 includes a white light source 212, an illumination lens 213, the half mirror 214, and the objective lens 202.

In the bright-field illumination optical system 211, the illumination lens 213 converts the white illumination light emitted from the white light source 212 into parallel light. The half mirror 214 turns back half of the incident parallel light to the direction parallel to the optical axis of the detection optical system 210. The light is then condensed on the observation region, and irradiated by the objective lens 202. It is possible to use the dichroic mirror in place of the half mirror 214, which is capable of transmitting more scattered light to the detector 207. In the case where the bright-field illumination optical system 211 is not used for the purpose of allowing more scattered lights to reach the detector 207, the half mirror 214 may be made movable so as to be detached from above an optical axis 301.

The detection optical system 210 includes, as shown in FIG. 2, the objective lens 202, lens systems 203, 204, a spatial distribution optical element 205, an imaging lens 206, and the detector 207.

In the above-structured detection optical system 210, the objective lens 202 collects the scattered light and reflecting light generated from the region on the sample 101 irradiated with the light from the dark-field illumination optical system 201 or the bright-field illumination optical system 211. The collected light is imaged on the detector 207 by the lens systems 203, 204 and the imaging lens 206. The light imaged by the detector 207 is converted into the electric signal, which is output to the control system 125. The signal processed by the control system 125 is stored in the storage device 124. The processed results or the stored processing results are displayed by the user interface 123.

The spatial distribution optical element 205 disposed on a pupil plane 302 of the detection optical system 210, or a pupil image 303 imaged by the lens systems 203, 204 selects the light to be detected by the detector 207 from those collected by the objective lens 202, and controls the polarization direction. Additionally, a switching mechanism 208 disposes the spatial distribution optical element 205 suitable for detection of the subject defect from the plurality of spatial distribution optical elements 205 having different optical characteristics on the optical axis 301 of the detection optical system 210.

The spatial distribution optical element 205 is not necessarily disposed on the optical axis 301. In such a case, a dummy substrate which changes the optical path length the same with that of the optical element 205 is disposed on the optical axis 301. The switching mechanism 208 is capable of switching between the optical element 205 and the dummy substrate. For example, in the case of the bright-field observation, or no optical element 205 suitable for the observation object, the optical element 205 may cause the risk of deterioration in the image acquired by the detector 207. If the optical element 205 is not used, it is preferable to dispose the dummy substrate on the optical axis 301. Patent Literature 1 describes the optical element 205 in detail.

The control system 125 selects the spatial distribution optical element 205 suitable for detection of the subject defect from the user interface 123 or outputs of the defect inspection device 107, and executes switching operation of the spatial distribution optical element 205. The control system 125 controls a height control mechanism 209 to coincide the focal point of the detection optical system 210 with the observation region on the sample 101. The linear stage, ultrasonic motor, piezo stage, and the like may be employed as the height control mechanism 209. The two-dimensional CCD sensor, the line CCD sensor, the TDI sensor group including a plurality of TDIs arranged parallel to one another, photodiode array and the like may be employed as the detector 207. The detector 207 is disposed so that its sensor surface has a conjugate relationship with the surface of the sample 101 or the pupil plane 209 of the objective lens.

Described is the process flow from defect detection executed by the defect inspection device 107 as the additional inspection device to the defect observation executed by the defect observation device 1000. The defect inspection device 107 as the additional inspection device is used for detecting the defect on the sample 101, and outputs the defect information to the storage device 124, or the control system 125. The defect information of the sample 101 output from the defect inspection device 107 is constituted in accordance with the defect inspection conditions including any one of the defect inspection results such as the defect coordinate, defect signal, defect shape, polarization of the defect scattered light, defect type, defect label, defect feature amount, scattered signal on the surface of the sample 101, or combination thereof, and any one of illumination incident angle, illumination wavelength, illumination azimuth, illumination intensity, illumination polarization of the defect inspection device 107, azimuth/elevation angle of the detector 207, and detection region of the detector 207, or any combination thereof. In the case where information of a plurality of the detectors exists in the defect information acquired by the defect inspection device 107, the defect information of the sample 101 output for each of the sensors, or the defect information of the sample 101, formed by integrating the plurality of sensor outputs may be used.

The review device 100 is used for observing a part or all of the defects detected by the defect inspection device 107. At this time, based on the defect information acquired by the defect inspection device 107, the optical microscope 105 detects the defect position information again, which is converted into the position information on the review device 100. The stage 103 is moved in reference to the converted position information for positioning the observation defect in the observation view of the SEM 106. Then electron beam of the SEM 106 is focused to observe the defect. If needed, the defect image may be acquired, and the defect classification may further be executed by the SEM 106. Before observation using the SEM 106, it is possible to focus the electron beam in reference to the SEM image as required. This ensures to improve accuracy in focusing the electron beam of the SEM 106.

The demand of high integration conforming to advancement of the semiconductor process has micronized the defect causing critical damage to the semiconductor device. As the defect to be observed by the review device 100 is micronized, it is necessary to observe and image the micronized defect with higher magnification. In the case of using the review device 100 for in-line inspection of the semiconductor production, reduction in the observation period may shorten the tact time. The user of the review device 100 may demand quick observation and imaging of the defect through the SEM with both high resolution and high magnification.

As the defect to be observed by the review device 100 is micronized, the minimum defect size which can be detected by the optical microscope 105 has to be further reduced. In this context, the optical microscope 105 is configured to shorten the illumination light wavelength, actualize super resolution using spatially modulated illumination, attain high NA (Numerical Aperture) of the detection lens and the like. The device, however, allows reduction in the illumination light wavelength in the restrictive way. The numerical aperture (NA) of the detection lens in the atmosphere is approximately 1.0. The liquid immersion exposure method which actualizes the NA set to 1.0 or more, which has been implemented in the exposure process is not practically available for the semiconductor inspection.

The super resolution technique has received the attention for attaining high sensitivity of the optical microscope. Patent Literature 2 discloses the super resolution optical microscopic technique by means of standing wave illumination. The super resolution technique disclosed in the patent literature 2 irradiates the sample surface with two beams for interference thereon so as to form the intensity pattern having the periodically variable intensity distribution on the sample. Then the relative optical path length between the two beams is changed for phase modulation so as to spatially modulate the illumination intensity pattern. The spatially modulated illumination intensity pattern is used to acquire a plurality of signals each indicating the different illumination state derived from the light generated in the observation region. The use of the acquired signal ensures to generate the image with resolution higher than the acquired signal.

The standing wave illumination with periodic intensity variation both in the X-direction and Y-direction, and the phase modulation mechanism with respect to the X-direction and Y-direction are required for high resolution in two-dimensional direction utilizing the super resolution technique. It is also necessary to switch the illumination in the direction between the X-direction and Y-direction. Satisfying the needs, however, enlarges the size and cost of the illumination optical system of the optical microscope as well as reduce the throughput. The super resolution technique as disclosed in Patent Literature 2 cannot be applied to the optical microscope of line illumination scan type using narrow ray illumination intended to improve illumination intensity per unit area, and reduce noise such as scattered light in the background. It is also difficult to apply the super resolution technique because of significantly long time period is need for acquiring the image.

Aiming at addressing the above-described problem, the example is configured to allow the stage 103 to slightly shift the sample 101 in the Y-direction, and the dark-field illumination optical system 201 to modulate the illumination intensity pattern on the sample 101 in one-dimensional direction (X-direction). The detector 207 capable of observing a plurality of different observation regions collects the lights generated by the illumination intensity pattern for conversion into the electric signals. Using the electric signal, the control system 125 generates the electric signal with two-dimensionally higher spatial resolution than the original signal, or the image generated in accordance with the electric signal.

The example is configured to shift the relative intensity distribution of the illumination intensity pattern with respect to the observation region (hereinafter, referred to as relative intensity distribution) in two-dimensional direction for the super resolution process in the two-dimensional direction so as to acquire the signal from the sample 101. Specifically, the optical element such as the mirror in the dark-field illumination optical system 201 is driven by the piezo element, for example, for sequential slight shifting to change the optical path length so that the illumination intensity pattern on the sample 101 is shifted in the one dimensional direction (X-direction) (hereinafter, referred to as illumination phase shift). The stage 103 is driven for slightly shifting the sample 101 sequentially in the Y-direction so that the illumination intensity pattern is shifted in the Y-direction that is different from the X-direction in which the illumination intensity pattern is shifted by the dark-field illumination optical system 201 (hereinafter, referred to as sample scan). The sample scan allows shifting of the imaging position on the detector 207 via the arbitrary coordinate (x, y) in the observation region.

The control system 125 selects the signal used for the super resolution process from the shift amount by the sample scan, and calculates the resolution using the selected signal. The detector 207 may be constituted by the plurality of two-dimensional sensors, or line sensors disposed in the direction orthogonal to the sample scanning direction so as to be arranged parallel to one another. In this case, the pitch between the line sensors and the minimum number of the line sensors are determined in accordance with the shift amount of the sample scanning.

The TDI sensor (Time Delay Integration Sensor), line CCD (Charge Coupled Device) sensor, one-dimensional photodiode array and the like may be employed for the line sensor. The two-dimensional CCD, the two-dimensional photo diode array and the like may be employed for the two-dimensional sensor. For example, in the case of using the line sensors, the respective imaging regions do not have to be adjacent to each other.

The illumination is preliminarily shifted with respect to the sample for calibration to acquire the intensity variation in the respective imaging regions. The initial phase difference of the illumination distribution between the imaging regions may be derived from the acquired intensity variation. The use of the acquired information allows setting of the respective imaging regions so that the initial phase difference becomes suitable for acquisition of the high resolution image.

The single sensor may be sufficient for constituting the two-dimensional sensor. In this case, a plurality of two-dimensional signals (three or more) each imaged at different time are acquired. Signals from the same point on the sample are extracted. The use of the signals from the same points on the sample, imaged at the plurality of different times allows acquisition of the high resolution signal.

Figure 10:
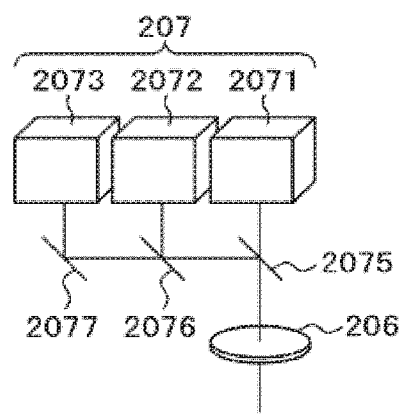
FIG. 10 is a block diagram schematically illustrating a structure of a detector of the optical microscope according to the first and the third examples of the present invention.

A plurality of TDI sensors to be employed are arranged to form the view with different illumination intensity phases. In the case of difficulty in spatial arrangement of the plurality of TDI sensors, a beam splitter 2075 that transmits ⅓ of the incident light and reflects ⅔ thereof, and half mirrors 2076, 2077 are combined as shown in FIG. 10 so as to split the optical path into three. This makes it possible to arrange the plurality of TDI sensors (three in FIG. 10) 2071, 2072, 2073.

In the structure as described above, the beam splitter 2075 is configured to transmit ⅓ of the incident light, and reflect ⅔ thereof. The beam splitter 2075 may be replaced by the half mirror which reflects ½ of the incident light and transmits ½ thereof in the case of the same amount of each of illumination lights irradiated to the sample 101 from the three directions.

The illumination intensity pattern (hereinafter, two-dimensional intensity pattern) is required to have periodic intensity variation in two-dimensional direction for changing the relative intensity distribution in two-dimensional direction using the illumination phase shifting and the sample scanning. For example, the two-dimensional intensity pattern may be generated by interference of a plurality of illuminations each in the different incident plane. Another method may be implemented by projecting a slit image with periodic structure in two-dimensional direction onto the sample 101.

The two-dimensional intensity pattern resulting from interference of the illumination light is allowed to shorten the intensity varying period so as to synthesize the signal with higher resolution. Meanwhile, the two-dimensional intensity pattern resulting from the slit image projection is capable of using the light with no interference and the broadband light so as to actualize the stable illumination system highly resistant against the surface property of the sample 101, and the environmental change. The process for forming the two-dimensional intensity pattern has to be selected in accordance with the inspection environment.

The structured illumination microscopy (SIM, hereinafter referred to as structured illumination) with high defect detection sensitivity is applied to the super resolution optical microscope to one-dimensionally reduce the illumination phase shift direction. The simply configured illumination optical system actualizes compact size of the optical microscope, cost reduction, and further reduction in the defect detection time period. Compared with the review device having the super resolution optical microscope provided with the interference optical system, and the phase shift mechanism in two-dimensional direction, the example is capable of actualizing high sensitivity, compact size, cost reduction, and high throughput.

FIG. 4 represents an illumination intensity pattern on the surface of the sample 101 of the optical microscope 105. The sample scanning and the illumination phase shifting on the surface of the sample 101 of the optical microscope 105 will be described referring to FIG. 4. FIG. 4 represents the use of the plurality of TDI sensors for the detector 207. However, it is also possible to employ the two-dimensional sensor.

The illumination light emitted from the illumination light source inside the dark-field illumination optical system 201 is split thereby into three lights 321a, 321b, 321c, each of which is incident on the observation region on the sample 101 at different incident angles so as to generate a two-dimensional intensity pattern 328 on the sample 101. The two-dimensional intensity pattern 328 is shifted by the phase shifting of the light 321b in an X-direction 332. A sample scan direction 327 corresponds to a Y-direction 331 that is different from the X-direction 332.

Observation regions 323, 324, 325 on the sample 101 of the plurality of TDI sensors are directed perpendicularly to a sample scanning direction 327, and arranged therealong. An arbitrary coordinate 326 on the sample 101 exists at a point 326a at a time $t_0$, and moves to a point 326b at the time $t_1$, and further to a point 326c at the time $t_2$ through the sample scanning. The sample scanning may vary the illumination intensity in the Y-direction 331 with respect to the arbitrary coordinate 326. The respective TDI sensors will detect the light generated at the arbitrary coordinate 326 at the different time under the illumination with different intensity. This makes it possible to change the relative intensity distribution in the Y-direction 331. It is necessary to synchronize the scan speed with the signal acquiring timing of the TDI sensor.

The sample scanning and the illumination phase shifting may be executed either simultaneously or individually. If they are executed individually, the required number of signals in the Y-direction 331 are acquired by sample scanning, and the optical path length of the light 321b is changed so as to shift the illumination phase by one step. Then the required number of signals in the Y-direction 331 are acquired again by sample scanning. The above-described steps are repeatedly executed until the required number of times of illumination phase shift is attained. The two-dimensional intensity pattern modulated in the X-direction 332 and the Y-direction 331 allows the detector 207 to detect the light generated on the sample 101. Alternatively, it is possible to acquire the required number of signals in the Y-direction 331 by sample scanning after acquisition of the required number of signals in the X-direction 332 by illumination phase shifting.

Described is the method of illumination phase shift of the two-dimensional illumination pattern generated by interference among a plurality of light beams referring to FIG. 3B. FIG. 3B only shows the single light beam. FIG. 3B omits showing the lens system for forming the illumination light and filters.

As described referring to FIG. 3A, the illumination light emitted from the light source 231 has the optical path split into three each with the same light amount by the beam split section 236b including the reflector 2361 and the half mirror 2362. The split illumination lights into three optical paths are incident on the respective illumination systems 201a to 201c for irradiation onto the sample 101.

As described referring to FIG. 3B, the method of displacing the mirrors 2014a to 2014c may be employed for changing the optical path length of the light 321 irradiated onto the sample 101. For example, the mirror 2014a of the illumination system 201a is driven by the piezo element 2015a in the arrow direction for slight shifting by the magnitude corresponding to several wavelengths of the illumination light so as to change the optical path length of the illumination light 321 up to the surface of the sample 101.

Another method for changing the optical path length of the illumination light 321 may be implemented by the piezo element 2016a which drives the step-like parallel flat plate 2012a made of material with refractive index different from that of air, which is disposed on the optical path of the illumination system 201a in the arrow direction for displacement. The step-like parallel flat plate 2012a allows stepwise change in the optical path length.

FIG. 3B shows the piezo element 2015a which displaces the mirror 2014a, and the piezo element 2016a which displaces the step-like parallel flat plate 2012a for explanatory purpose. However, it is possible to employ only one of those piezo elements. FIG. 3B illustrates the illumination phase shift method with respect to the single light beam. The phase shift mechanism is not necessarily required for all the split light beams, respectively. In the case of three-wave interference as shown in FIG. 3A, it is sufficient to provide the phase shift mechanism only on the optical path of the illumination system 201a.

The illumination phase shift method with respect to the two-dimensional illumination pattern generated by the slit image projection may be implemented by displacing the slit or the optical element that constitutes a projection optical system for projecting the slit image. The piezo stage and the linear stage may be employed for the method of driving the mirror 2013a and the parallel flat plate 2012a in the thus structured phase shift mechanism.

Alternatively, the method of shifting the illumination phase of the two-dimensional illumination pattern may be implemented by controlling the voltage applied to the electro-optic crystal on the optical path, having the reflectivity changed at the applied voltage so as to change the optical path length of the light 321a.

Figure 5:
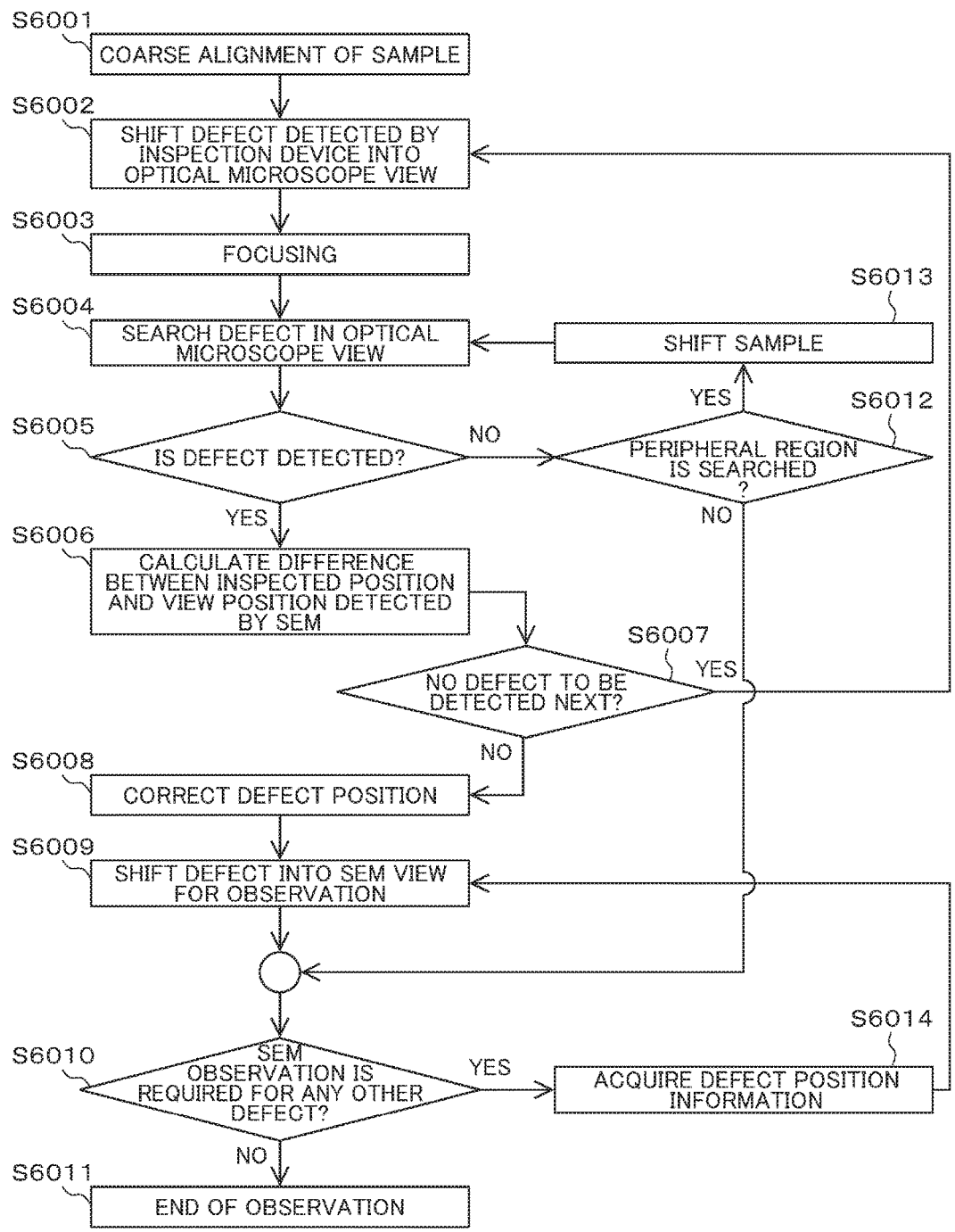
FIG. 5 is a flowchart representing a process flow of defect observation performed by the defect observation device according to the first example of the present invention.

FIG. 5 is a flowchart representing process steps up to the defect observation according to the first example.

The defect information of the sample 101, which has been output from the external inspection device 107 is read. Based on the defect information, the defect is observed by the review device 100. Upon observation of the defect, the sample 101 is irradiated by the bright-field illumination optical system 211 of the optical microscope 105 for the bright field observation performed by the detection optical system 210 or another microscope for alignment purpose so that the coarse alignment of the sample 101 is performed (S6001). Then based on the read defect information of the sample, which has been output from the external inspection device 107, the stage 103 is moved to bring the observation defect into the view of the optical microscope 105 (S6002). The height control mechanism 209 moves the objective lens 202 of the optical microscope for focusing the optical microscope 105 on the sample 101 (S6003).

The image around the observation region is acquired by the optical microscope 105. Based on the acquired image, the defect to be observed is searched (S6004). Upon detection of the observation defect based on the acquired image (S6005—YES), the difference between the defect detection position derived from the optical microscope 105, and the defect position detected by the inspection device 107 is calculated (S6006).

Meanwhile, if the observation defect cannot be detected in reference to the acquired image (S6005—NO), the defect is considered to be out of the view of the optical microscope 105. It is possible to image the peripheral area of the imaging region by the optical microscope 105 for searching the observation defect. Upon imaging of the peripheral area of the view (S6012—YES), the stage 103 is moved by the amount corresponding to the view of the optical microscope 105 (S6013) to return to step (S6004) for defect detection by the optical microscope 105 for further proceeding the process.

If there is no defect to be detected by the optical microscope 105 (S6007—NO), the observation defect position is converted into the position coordinate on the review device (S6008). The stage 103 is moved to bring the observation defect into the view of the SEM 106, and the electron beam is focused on the sample 101 so as to acquire the SEM image (S6009). Meanwhile, if there is the defect to be detected next (S6007—YES), the process returns to step (S6002) for the defect detection by the optical microscope 105 in the review device as described above for proceeding the process.

After acquisition of the SEM image, the control system 125 determines whether there is the defect to be observed next (S6010). If there is the defect to be observed (S6010—YES), the corrected position information of the defect to be observed next is acquired (S6014). The process returns to step (S6009) for the defect observation by the review device as described above for proceeding the process. Meanwhile, if there is no defect to be observed next (S6010—NO), the observation by the review device 100 ends (S6011).

FIG. 5 shows the process flow in which all the coordinates of the plurality of observation defects are acquired by the optical microscope 105 so that the defects derived from the coordinate are observed by the SEM 106. The process flow may be implemented by repeatedly executing steps of acquiring the coordinate of the single observation defect so as to be observed by the SEM 106, acquiring the coordinate of the next observation defect for observation, and the like.

Figure 6:
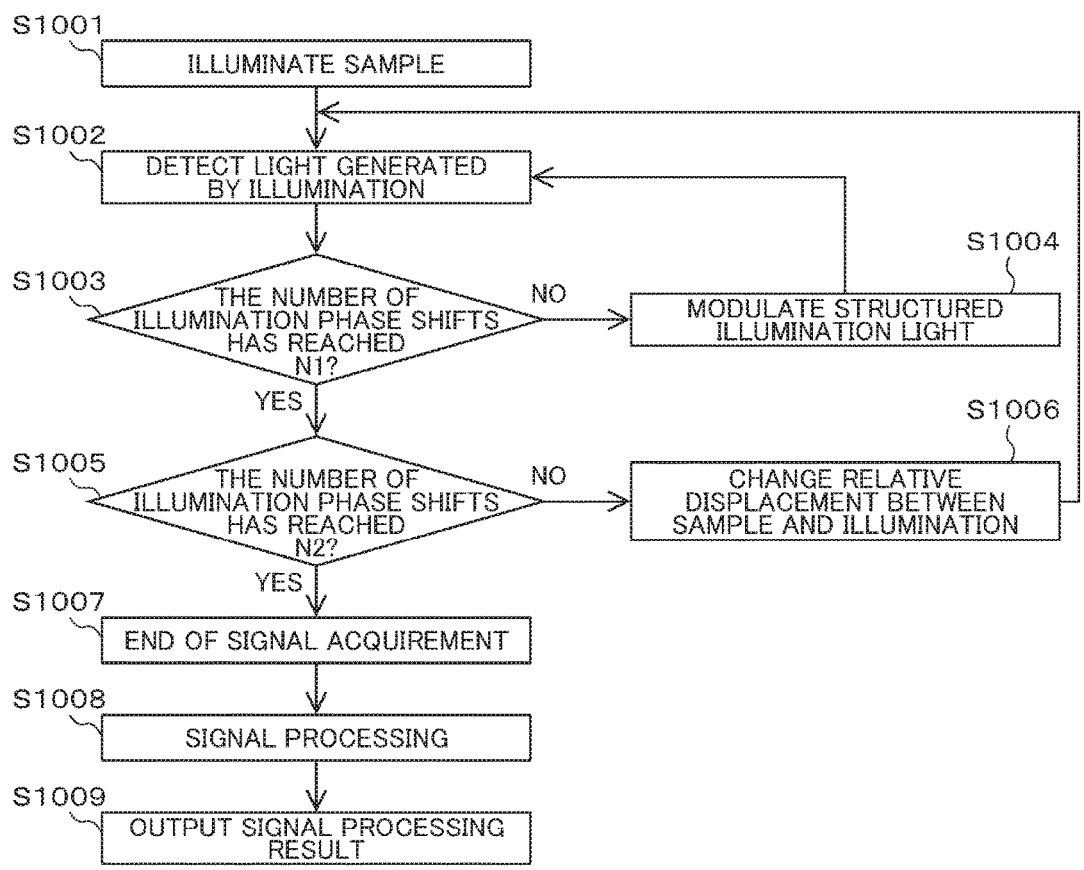
FIG. 6 is a flowchart representing a process flow of defect detection using the optical microscope of the defect observation device according to the first example of the present invention.

FIG. 6 shows the process flow executed by the optical microscope 105 in the review device 100 up to the defect detection according to the first example. The illumination lights (laser) 321*a*, 321*b*, 321*c* emitted from the three illumination systems 201*a*, 201*b*, 201*c* of the dark-field illumination optical system 201 (FIG. 2) are irradiated to the observation region of the sample 101 from three directions (S1001). Then the light generated by the illumination lights on the sample surface is detected by the detector 207 of the detection optical system 210 (S1002). The illumination phase is shifted until the number of the illumination phase shifts reaches the predetermined number $N_1$ (S1003—NO) for modulating the structured illumination on the observation region (S1004). The detector 207 detects the light generated by the modulated illumination from the sample (S1002).

After the illumination phase shifts performed $N_1$ times (S1003—YES), the stage 103 is driven to slightly shift the sample 101 in the direction 327 (Y-direction) for sample shifting once to change the relative position between the sample and illumination (S1006). The process returns to step (S1002) for detecting the light generated from the sample by the detector 207 while shifting the illumination phase as described above for proceeding the process. Then if the number of sample shifts has reached the predetermined number of the sample shifts $N_2$ (S1007), the signal acquisition ends (S1007).

The control system 125 processes the plurality of acquired signals for synthesizing the high resolution signal so as to obtain the defect coordinate (S1008). Finally, the control system outputs the signal processing result such as the synthesized high resolution signal, and the obtained defect coordinate (S1009).

The order of executing steps of S1003, S1005, and S1006, S1004 may be inverted. Specifically, after the number of sample shifts reaches $N_2$, the illumination phase shift is executed once, which will be repeatedly executed until the number of times of the illumination phase shift reaches $N_1$.

In order to synthesize the high resolution signals, it is necessary to focus the detection optical system 210 onto the sample 101 upon detection of the light generated from the sample 101 by the two-dimensional illumination pattern (S6003 in FIG. 5). The method for focusing as descried above may be implemented by the process using the illumination distribution on the sample 101, the process that allows the illumination lights 321*a*, 321*b*, 321*c* to use change in the position of the reflecting light from the sample 101, and the process that uses the predetermined measurement result of the optical height detector 104. Although not shown, the process using light, for example, interference type laser displacement gauge, or the process using the height measurement result from the electrostatic capacitance sensor may be applied.

Specifically, in the process using the illumination distribution on the sample 101, in the case of no pattern change in the view of the optical microscope 105, the detector 207 measures the intensity distribution in the illumination light field, and the stage 103 is moved so that the spatial change in the measured intensity distribution is coincided with the spatial change in the illumination distribution upon focusing for setting the focal position.

As the position of the light reflecting on the sample 101 changes in accordance with height of the sample 101, the process utilizing change in the reflecting position of the reflecting light is executed by measuring the reflecting light position performed by the sensor so as to obtain the height of the sample 101. For example, the optical height detector 104 for measuring height of the view of the optical microscope 105 may be disposed. Alternatively, using the optical height detector 104 for measuring the height of the view of the SEM 106 to measure height of the desired coordinate on the sample 101 preliminarily for focusing the optical microscope 105 using the measurement result.

The example is configured to allow installation of the super resolution optical microscope provided with the interference optical system and the phase shift mechanism in the two-dimensional direction in the review device, thus attaining high sensitivity, compact size, and high throughput.

Example 2

A second example of the present invention will be described. The review device of this example has the same structure as the one described in the first example referring to FIGS. 1 to 3B. The explanation of the device structure, thus, will be omitted. This example is different from the first example in that the illumination phase shift and the sample shift are executed simultaneously. The operation that is different from the one as described in the first example will be explained hereinafter.

Figure 7:
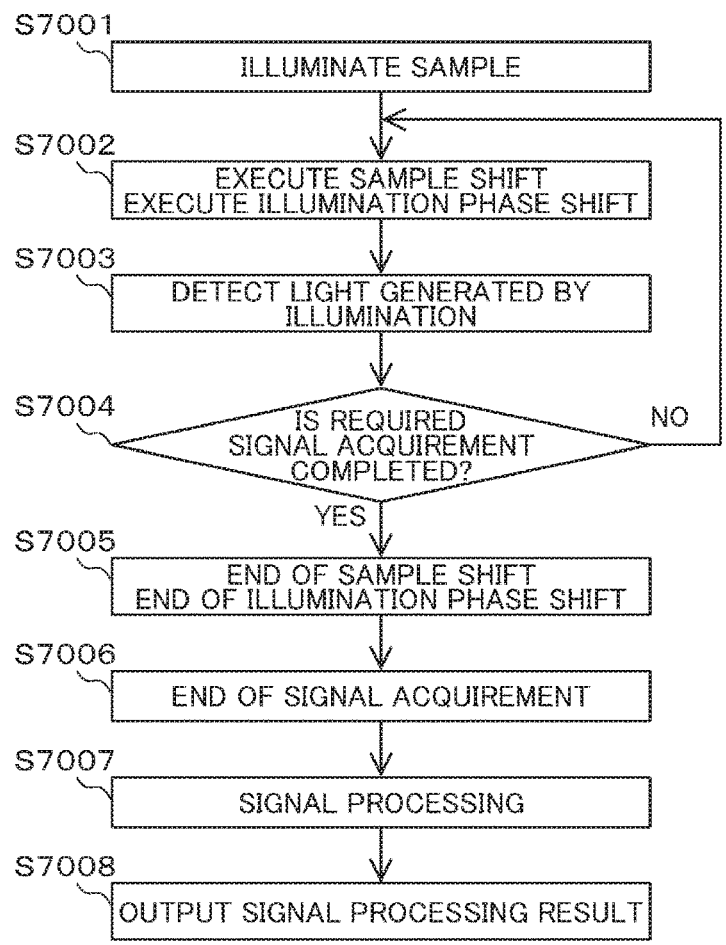
FIG. 7 is a flowchart representing a process flow of defect detection using the optical microscope of the defect observation device according to a second example of the present invention.

FIG. 7 is a flowchart showing the process flow executed by the optical microscope in the review device up to the defect detection according to the second example. This flowchart corresponds to the one described in the first example referring to FIG. 6. The structure of the review device will be described referring to FIGS. 1 to 3B.

The illumination lights 321*a*, 321*b*, 321*c* emitted from the three illumination systems 201*a*, 201*b*, 201*c* of the dark-field illumination optical system 201 are irradiated to the observation region of the sample 101 (S7001). Then the illumination phase is shifted and sample scanning is executed while modulating the structured illumination on the observation region (S7002). The detector 207 detects the light (scattered light) generated on the sample 101, fluctuated by the modulated structured illumination (S7003). Steps of the illumination phase shift and the sample shift (S7002), and detection of the light generated on the sample 101 (S7003) will be repeatedly executed until the respective numbers of the illumination phase shifts and the sample shifts reach the predetermined numbers $N_1$ and $N_2$ (S7004—NO).

After acquiring the required number of signals (S7004—YES), the process stops execution of the illumination phase shift and the sample shift (S7005) as well as the signal acquisition (S7006). The signal is processed while following the procedures (S7007), and the signal processing result is output (S7008). The sample scanning is executed in accordance with the step-like displacement or slope-like displacement. The intensity modulation for the illumination phase shift of the structured illumination is executed in the direction different from the sample scanning direction.

This example ensures to apply the super resolution technique of illumination modulation type to the line scanning method, attain high intensity/density of illumination, and improve the defect detection sensitivity.

Example 3

Figure 9:
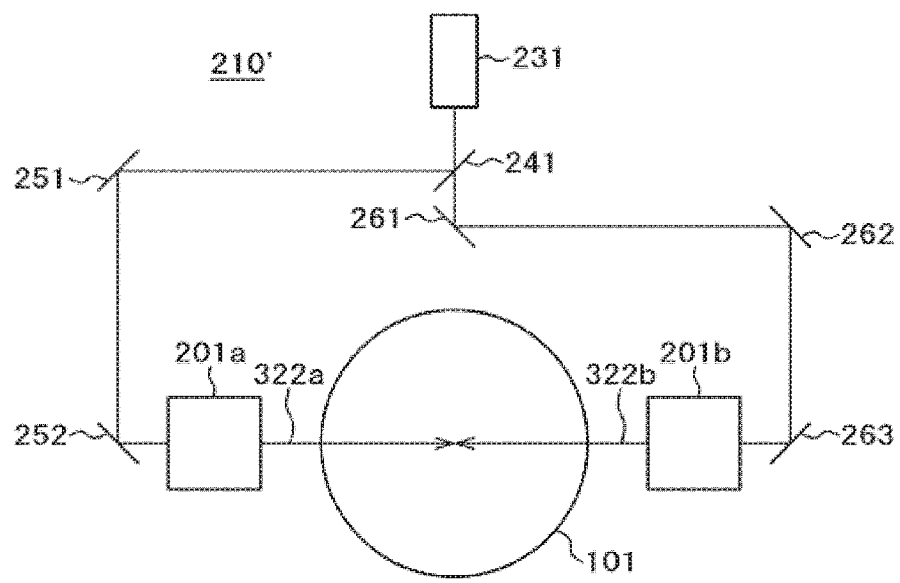
FIG. 9 is a block diagram schematically illustrating a dark-field illumination optical system of the optical microscope according to the third example of the present invention.

A third example will be described with respect to the high resolution signal processing in one-dimensional direction. The optical microscope of this example has basically the same structure as the one described in the first example referring to FIG. 2. The explanation of the device structure, thus, will be omitted. Unlike the structure of the dark-field illumination optical system 201 as described referring to FIG. 3A, the dark-field illumination optical system 210' as shown in FIG. 9 is configured to illuminate the surface of the sample 101 from two directions opposite to each other, and the detector 207 of the detection optical system 210 is constituted by three detectors 2071, 2072, 2073 as shown in FIG. 10.

The dark-field illumination optical system 201' according to the example includes a light source 231 for emitting laser beams, a half mirror 241, mirrors 251, 252, 261, 262, 263, and illumination systems 201a, 201b. In the dark-field illumination optical system 201', the half mirror 241 splits the optical path of the illumination light (laser) emitted from the light source 231 into two. The illumination light reflected by the half mirror 241 is reflected by the mirrors 251 and 252, which is then incident on the illumination system 201a. The illumination light irradiates the surface of the sample 101 as an illumination light 322a from the arrow direction. Meanwhile, the illumination light that has transmitted through the half mirror 241 is reflected by the mirrors 261, 262, 263, and incident on the illumination system 201b. The illumination light then irradiates the surface of the sample 101 as an illumination light 322b from the arrow direction.

The light transmitting through the imaging lens 206 has its ⅓ transmitting, and ⅔ reflected by the beam splitter 2075. The light which has transmitted through the beam splitter 2075 is detected by the detector 2071.

Meanwhile, the light reflected by the beam splitter 2075 is incident on the half mirror 2076, allowing half of the incident light to transmit, and another half to be reflected. The light reflected by the half mirror 2076 is detected by the detector 2072.

The light transmitting through the half mirror 2076 is incident on the mirror 2077, and entirely reflected thereby so as to be detected by the detector 2073.

In the structure as described above, the beam splitter 2075 transmits ⅓ of the incident light, and reflects ⅔ thereof. However, the beam splitter 2075 may be constituted by the half mirror which reflects ½ of the incident light, and transmits ½ thereof.

If the spatial resolution of the detection optical system differs in accordance with the direction, the example is applied for the purpose of improving the resolution at the low resolution side. Specifically, the pupil surface of the detection optical system of the optical microscope is partially shielded with the spatial mask and the like in order to eliminate the diffraction light due to pattern, and defective scattered light that is unnecessary for the detection. Deviation in the shielding region of the pupil surface between the X-direction and the Y-direction results in the resolution difference therebetween.

Figure 8:
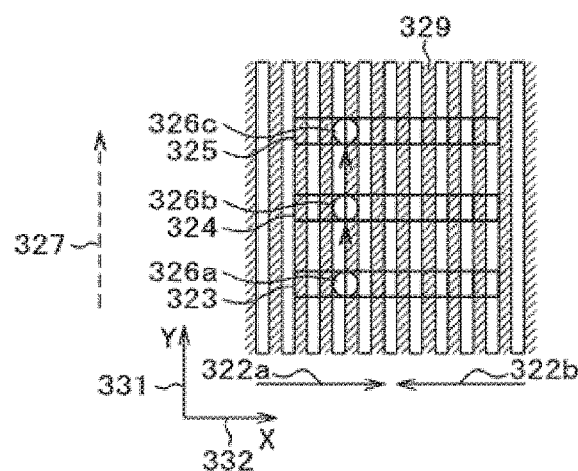
FIG. 8 is a plan view of the sample, indicating an illumination intensity distribution on the sample surface by the dark-field illumination of the optical microscope according to a third example of the present invention.

FIG. 8 shows an illumination intensity pattern on the surface of the sample placed in the optical microscope. The resolution increase in the direction (=X-direction 332) different from the direction 327 in which the sample is shifted will be described referring to FIG. 8. FIG. 8 shows the use of the plurality of TDI sensors for constituting the detector 207. However, the two-dimensional sensor may be used. The two illumination lights 322a and 322b from the dark-field illumination optical system 201' are incident on the observation region on the sample 101 each at the incident azimuth opposite to each other so that a standing wave pattern 329 is generated on the sample 101.

At the arbitrary time point, the standing wave pattern 329 has no periodic intensity variation with respect to the direction 327 (Y-direction) in which the sample is shifted, while having the periodic intensity variation with respect to the X-direction 332. The standing wave pattern 329 ensures to allow the three TDI sensors 2701, 2702, 2703 which constitute the detector 207 to detect the lights generated from the sample 207 by the observation regions 323, 324, 325 of the detector 207, and convert into electric signals.

Each of the observation regions 323, 324, 325 of the three TDI sensors 2701, 2702, 2703 which constitute the detector 207 has the view in the different area within the observation region. The standing wave pattern 329 is shifted in the X-direction 332 by the phase shift of the light 321a or 321b. The direction 327 in which the sample is shifted is the Y-direction 331 that is different from the X-direction 332. The three TDI sensors 2701, 2702, 2703 are arranged so that the observation regions 323, 324, 325 on the sample 101 are directed perpendicularly to the direction 327, in which the sample is shifted therealong.

As the sample is shifted, the arbitrary coordinate 326 on the sample 101 that exists at the point 326a at the time $t_0$ will move to pass the point 326b at the time $t_1$, and the point 326c at the time $t_2$. The illumination phase shift is executed simultaneously with the sample shifting so as to acquire the plurality of lights generated on the sample 101, which have been acquired by the phase shifted standing wave pattern 329 at the arbitrary coordinate 326.

Specifically, along with passage of the arbitrary coordinate 326 to 326a, 326b, and 326c, the illumination phase is shifted so as to change each of the illumination intensities at the respective coordinates 326a, 326b, and 325c.

The present method is not capable of improving the resolution in the direction 327 in which the sample is shifted because there is no periodic intensity variation in the structured illumination in the sample shifting direction 327. However, the present method ensures to set the long storage time of the detector 207 as well as high sensitivity by changing the distance of the observation region and the sample shifting speed. This makes it possible to apply the super resolution technique of illumination modulation type to the line scanning method which continuously shifts the sample for inspection. This may further attain high intensity/density of illumination, and improve detection sensitivity.

The process flow executed by the optical microscope in the review device up to the defect detection according to the third example is similar to the one according to the second example as described referring to FIG. 7.

Example 4

A fourth example of the present invention will be described referring to FIGS. 11 and 12. In this example, the structure of the review device is basically the same as the one according to the first example described referring to FIGS. 1 to 3B. The explanation of the device structure, thus, will be omitted. The dark-field illumination optical system has the same structure as that of the dark-field illumination optical system 201' according to the third example as described referring to FIG. 9.

Figure 11:
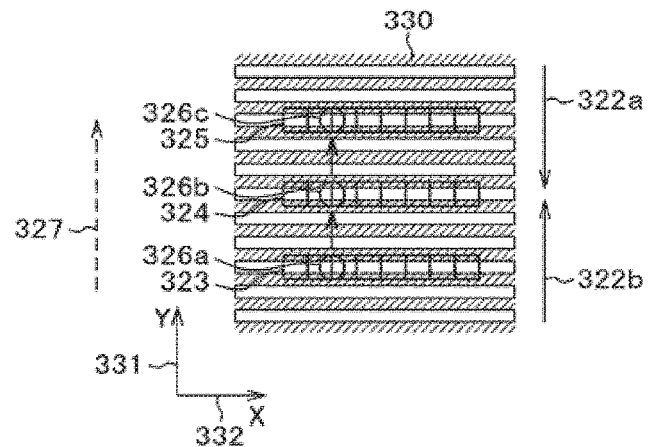
FIG. 11 is a plan view of the sample, indicating an illumination intensity distribution on the sample surface by the dark-field illumination of the optical microscope according to a fourth example of the present invention.

FIG. 11 shows an illumination intensity pattern on the surface of the sample placed in the optical microscope. Described referring to FIG. 11 is the method of inspecting the surface of the sample in movement in the optical microscope upon increase in the resolution in the sample shifting direction 327. FIG. 11 shows the three TDI sensors 2701, 2702, 2703 constituting the detector 207 as described referring to FIG. 10. However, the detector 207 may be constituted by the single two-dimensional sensor in place of those sensors.

The illumination lights 322a, 322b emitted from the dark-field illumination optical system 201' are incident on the observation region on the sample 101 each at the incident azimuth opposite to each other so that a standing wave pattern 330 is generated on the sample 101. The standing wave pattern 330 has the periodic intensity variation in the Y-direction 331 unlike the standing wave pattern 329 as shown in FIG. 8, and has no periodic structural variation in the X-direction 332. Shift of the sample in the Y-direction 331 having the periodic intensity variation ensures to move the arbitrary coordinate 326 on the sample 101 to the points 326a, 326b, 326c. The lights generated at the respective positions are detected by the detector 207 including the respective detection regions 323, 324, 325 so as to modulate intensity of the illumination to the arbitrary coordinate 326.

Likewise the first example, for example, in the case of using the line sensor, the respective imaging regions do not have to be adjacent to one another. The initial phase difference in the illumination distribution between the respective imaging regions may be derived from shifting illumination to the calibration sample preliminarily so as to acquire the intensity variation in the respective imaging regions. The initial phase difference between the imaging regions may be derived from the acquired intensity variation. It is possible to set the respective imaging regions so that the initial phase difference is suitable for acquisition of the high resolution image.

Figure 12:
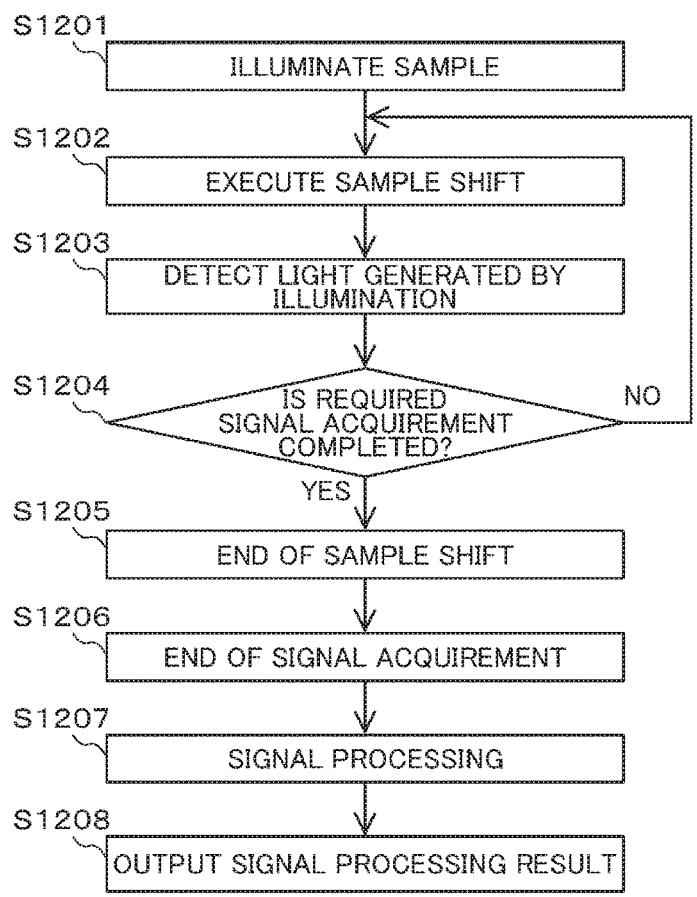
FIG. 12 is a flowchart representing a process flow of defect detection using the optical microscope of the defect observation device according to the fourth example of the present invention.

FIG. 12 is a flowchart executed by the optical microscope 105 in a review device 1000 up to the defect detection according to the fourth example. An illumination light emitted from the dark-field illumination optical system 201' is irradiated to the observation region of the sample 101 (S1201). Then the sample shift is started (S1202), and the light generated on the sample 101 in movement is detected by the detector 207 (S1203). Steps of sample shifting (S1202), and detection of the light generated on the sample 101 (S1203) are repeatedly executed until the number of executed sample shifts reaches the predetermined value $N_2$ (S1204—NO). After acquiring the required number of signals (S1204—YES), the sample shift ends (S1205), the signal acquisition ends (S1206), the processing is executed by following the procedure (S1207), and the signal processing result is output (S1208). The sample scanning is executed in accordance with the step-like displacement or the slope-like displacement.

The method of the example attains one-dimensional high resolution in the sample scanning direction, and eliminates the illumination phase shift mechanism, resulting in simply structured device.

According to the first, second, third, fourth examples, the structure using the interference light as the structured illumination has been described. However, it is possible to use the slit image projected as the structured illumination.

The present invention made by the inventor has been specifically described based on the examples. However, it is to be understood that the present invention is not limited to those examples, but may be arbitrarily configured without deviating from the scope of the invention.

REFERENCE SINGS LIST

101: sample,
102: sample holder,
103: stage,
104: optical height detector,
105: optical microscope,
106: electron microscope,
107: inspection device,
111: vacuum sealing window,
112: vacuum tank,
121: network,
122: library,
123: user interface,
124: storage device,
125: control system.

The invention claimed is:

1. A defect observation method comprising:
obtaining, from a storage device, position information of a defect on a sample;
optically detecting the defect on a sample using a detector of a defect observation device using said position information of the defect on the sample;
correcting the position information of the detected defect; and
observing the defect by a scanning electron microscope using the corrected position information, upon optical detection of the defect using the position information of the defect on the sample;
irradiating a same region on the sample having the defect with dark-field illumination lights from three directions, respectively, for interference with one another to generate an interference pattern having periodic intensity variation;
executing phase modulation of the interference pattern by slightly shifting an optical path length of the dark-field illumination system;
sample scanning by slightly shifting a stage on which the sample is placed, and irradiating the sample surface for illumination of the sample with an illumination intensity pattern having periodic intensity variation in a two-dimensional direction for shifting an imaging position on the detector; and
executing a super resolution process by selecting a signal used for the super resolution process from a shift amount derived from the sample scanning.

2. The defect observation method according to claim 1, wherein illumination of the sample with the illumination intensity pattern having periodic intensity variation in the two-dimensional direction includes steps of forming the illumination intensity pattern having periodic intensity distribution variation on the sample, and slightly shifting the sample sequentially in a direction different from the phase modulation direction while phase modulating the illumination intensity pattern.

3. The defect observation method according to claim 1, wherein illumination of the sample with the illumination intensity pattern having the periodic intensity variation in the two-dimensional direction is implemented by:
irradiating the defect with lights each having a same wavelength from different directions using said position information of the to generate an interference pattern on the sample surface having the defect;
periodically shifting the interference pattern generated on the sample surface in one-dimensional direction by periodically changing a relative phase of lights each with the same wavelength irradiated from the different directions; and
in a state where the interference pattern is periodically shifted in one-dimensional direction, slightly shifting the sample sequentially in one-dimensional direction different from the one-dimensional direction.

4. The defect observation method according to claim 1, wherein illumination with the illumination intensity pattern having periodic intensity variation in the two-dimensional direction is implemented by alternately repeating irradiation of the sample surface with illumination lights having phase modulated on the sample surface having the defect in one-direction, and irradiation of the sample surface with the illumination lights slightly shifted sequentially in a direction different from the one-direction.

5. A defect observation device comprising:
a stage on which a sample is placed;
an optical microscope configured to allow a detector of the defect observation device to optically detect a defect of the sample placed on the stage using position information of the defect;
a control system configured to correct the position information of the defect detected by the detector of the optical microscope; and
a scanning electron microscope which allows a scanning electron microscope to observe the defect using the corrected defect position information, wherein the optical microscope includes
an illumination light source, lens, and mirror which irradiate a same region on the sample having the defect with dark-field illumination lights from three directions for interference with one another to generate an interference pattern having periodic intensity variation;
a piezo element configured to perform phase modulation of the interference pattern generated by the illumination light source by slightly shifting optical path lengths of the dark-field illumination lights; and
a stage drive which slightly shifts the stage on which the sample is placed,
wherein the control system is further configured to slightly shift the stage on which the sample is placed by the stage drive while illuminating the sample with the illumination intensity pattern having periodic intensity variation in a two-dimensional direction, formed by the piezo element phase modulation of the interference pattern generated by the illumination light source, and to select a signal for a super resolution process from a shift amount derived from sample scanning of the illumination intensity pattern so as to execute the super resolution process using the selected signal.

6. The defect observation device according to claim 5, wherein:
the illumination light source, lens, and mirror are configured to execute phase modulation of the plurality of illumination lights in one direction by forming the illumination intensity pattern having periodic intensity distribution variation on the sample; and
the piezo element configured to perform phase modulation spatially modulates the plurality of illumination lights by slightly shifting the sample sequentially in a direction different from the phase modulating direction.

7. The defect observation device according to claim 6, further comprising a plurality of mirrors configured to relatively change optical path lengths of the plurality of illumination lights.

8. The defect observation device according to claim 5, wherein the sample is illuminated with the illumination intensity pattern having periodic intensity variation in the two-dimensional direction by alternately repeating irradiation of the sample surface with illumination lights having phase modulated in the one direction on the sample surface having the defect by the illumination light source, and irradiation of the sample surface with the illumination lights slightly shifted in a direction different from the one direction by the piezo element configured to perform phase modulation.

* * * * *